United States Patent [19]

Belisle

[11] Patent Number: 5,235,705
[45] Date of Patent: Aug. 17, 1993

[54] POCKET PORTABLE URINAL

[76] Inventor: Brice Belisle, 112 Conselyea St., Brooklyn, N.Y. 11211

[21] Appl. No.: 747,280

[22] Filed: Aug. 19, 1991

[51] Int. Cl.$^5$ .............................................. A47K 11/12
[52] U.S. Cl. ....................................... 4/144.3; 128/767; 604/350
[58] Field of Search .......................... 4/144.1–144.4; 604/349–352; 128/760, 767

[56] References Cited

U.S. PATENT DOCUMENTS

| 1,490,793 | 4/1924 | Ajamian et al. | 604/350 |
| 2,690,568 | 10/1954 | Willis | 4/144.4 |
| 2,699,781 | 1/1955 | Koch | 604/352 |
| 3,353,538 | 11/1967 | Carrigan | 604/352 |
| 3,559,651 | 2/1971 | Moss | 604/349 |
| 4,023,216 | 5/1977 | Li | 4/144.3 |
| 4,820,291 | 4/1989 | Terauchi et al. | 4/144.3 X |

FOREIGN PATENT DOCUMENTS

| 2060233 | 6/1972 | Fed. Rep. of Germany | 604/349 |
| 0667012 | 2/1952 | United Kingdom | 604/349 |

Primary Examiner—Charles E. Phillips

[57] ABSTRACT

A disposable pocket urinal is provided and consists of a waterproof flexible bag having an elongated neck portion to accommodate a penis from a male person so that the water proof bag can receive and retain urine during an emergency situation.

2 Claims, 1 Drawing Sheet

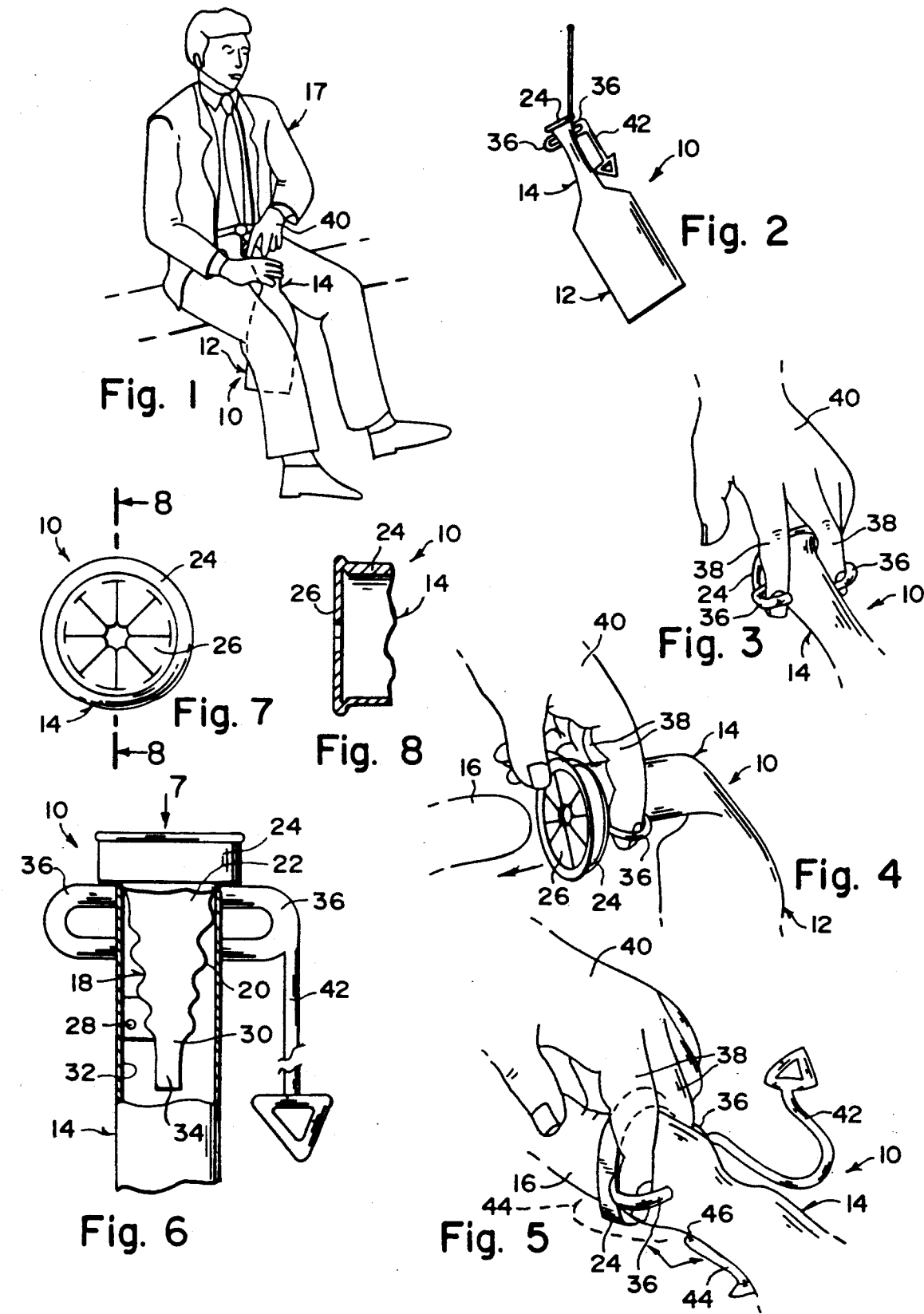

POCKET PORTABLE URINAL

BACKGROUND OF THE INVENTION

The instant invention relates generally to bedpans and more specifically it relates to a disposable pocket urinal which provides a sanitary mechanism for receiving and containing urine from a male in an emergency situation.

There are available various conventional bedpans which do not provide the novel improvements of the invention herein disclosed.

SUMMARY OF THE INVENTION

A primary object of the present invention is to provide a disposable pocket urinal that will overcome the shortcomings of the prior art devices.

Another object is to provide a disposable pocket urinal that is a waterproof bag with an elongated neck portion to accommodate different sized penises for receiving and retaining urine in an emergency situation.

An additional object is to provide a disposable pocket urinal having a funnel insert with a one way flap valve within the elongated neck portion and a closure seal in the upper end of the neck portion to prevent the back-up escape of the urine from the waterproof bag.

A further object is to provide a disposable pocket urinal that is simple and easy to use.

A still further object is to provide a disposable pocket urinal that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view showing the instant invention being used.

FIG. 2 is an elevational view of the invention per se.

FIG. 3 is a perspective view of the elongated neck portion and loop finger grips engaged by two fingers of a hand.

FIG. 4 is a perspective view of the elongated portion ready to be placed onto a penis.

FIG. 5 is a perspective view of a modified elongated neck portion on the penis, in which a foldable deflector member is connected underneath to catch any urine drippings therefrom.

FIG. 6 is an enlarged detail view with parts broken away of the elongated neck portion showing the flexible funnel member therein.

FIG. 7 is a top view taken in direction of arrow 7 in FIG. 6 showing the closure seal in the upper end of the elongated neck portion.

FIG. 8 is a cross sectional view taken along line 8—8 in FIG. 7.

DETAILED DESCRIPTION OF THE PREFERRED EMBODIMENTS

Turning now descriptively to the drawings, in which similar reference characters denote similar elements throughout the several views, the Figures illustrate a disposable pocket urinal 10 which consists of a water proof flexible bag 12 having an elongated neck portion 14 to accommodate a penis 16 from a male person 17 so that the water proof bag 12 can receive and retain urine during an emergency situation.

A flexible waterproof funnel member 18 having an undulating sinuous shaped tapered wall 20 is inserted within the elongated neck portion 14 of the flexible bag 12 with the wide upper end 22 of the flexible funnel member 18 attached to the upper end 29 of the elongated neck portion 14 to accommodate one of a plurality of different sized penises 16, so that as the penis 16 is pushed deeper into the flexible funnel member 18, the fit will become more and more snug to prevent urine leakage therefrom.

A waterproof closure seal 26 in the upper end 24 of the elongated neck portion 14 of the flexible bag 12, so that after the penis 16 is pushed into the flexible funnel member 18, the closure seal 26 will fit snugly about the penis 16 to prevent urine leakage therefrom. A spot heat seal 28 is placed between the narrow lower end 30 of the flexible funnel member 18 and the interior surface 32 of the elongated neck portion 14 of the flexible bag 12 in a conventional manner. A one way waterproof flap valve 34 is integrally formed on the narrow lower end 30 of the flexible funnel member 18 so that the one way flap valve 34 will prevent the back-up escape of the urine from within the flexible bag 12.

A pair of looped finger grips 36 are provided and are affixed oppositely to the elongated neck portion 14 of the flexible bag 14, below the upper end 24 thereof. The person 17 can extend two fingers 38 from their hand 40 into the looped finger grips 36 and pull the elongated neck portion 14 of the flexible bag 12 onto the penis 16. An elongated cord 42 extends from one of the looped finger grips 36 so that after using the disposable pocket urinal 10 the person 17 can wrap the elongated cord 42 through the looped finger grips 36 to tie off the elongated neck 14 of the flexible bag 12 for disposal thereof.

The disposable pocket urinal 10, as shown in FIG. 5, can further include a foldable deflector member 44 affixed at 46 onto the elongated neck portion 14 of the flexible bag 12. When the elongated neck portion 14 of the flexible bag 12 is pulled onto the penis 16, the foldable deflector member 44 can be flipped under the upper end 24 of the elongated neck portion 14 to catch any urine dripping therefrom.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A disposable pocket urinal which comprises a waterproof flexible bag having an elongated neck portion having an upper open end to accommodate a penis from a male person so that said waterproof bag can receive and retain urine during an emergency situation; further including a flexible waterproof funnel with a wide upper end and an undulating sinuous shaped tapered wall having a narrow lower end said funnel being inserted within the elongated neck portion of said flexible bag, with the wide upper end of said flexible funnel attached to the upper end of the elongated neck portion in a waterproof manner to accommodate one of a plurality of different sized penises, so that as the penis is pushed deeper into said flexible funnel the fit will become more and more snug to prevent urine leakage therefrom; further including;

means for attachment of said narrow lower end of said flexible funnel to said elongated neck portion of said flexible bag;

a one-way waterproof flap valve integrally formed on the narrow lower end of said flexible funnel so that said one-way flap valve will prevent back up of urine in said funnel;

a pair of spaced looped finger grips, disposed one on each side of said elongated neck portion of said flexible bag, so that the person can extend two fingers from their hand into said looped finger grips and pull the elongated neck portion of said flexible bag onto the penis; and an elongated cord extending from one of said looped finger grips so that after using said disposable pocket urinal the person can wrap said elongated cord through said looped finger grips to tie off the elongated neck of said flexible bag for disposal thereof.

2. A disposable pocket urinal as recited in claim 1, further including a foldable deflector affixed onto the elongated neck portion of said flexible bag so that when the elongated neck portion of said flexible bag is pulled onto the penis said foldable deflector can be folded under the upper end of the elongated neck portion to catch any urine dripping therefrom.

* * * * *